United States Patent [19]

Khosla et al.

[11] Patent Number: 5,049,493

[45] Date of Patent: Sep. 17, 1991

[54] ENHANCEMENT OF CELL GROWTH BY EXPRESSION OF A CLONED HEMOGLOBIN GENE

[75] Inventors: Chaitan S. Khosla; James E. Bailey, both of Pasadena, Calif.

[73] Assignee: California Institute of Technology, Pasadena, Calif.

[21] Appl. No.: 342,451

[22] PCT Filed: Oct. 21, 1988

[86] PCT No.: PCT/US88/03745

§ 371 Date: Jan. 24, 1989

§ 102(e) Date: Jan. 24, 1989

[87] PCT Pub. No.: WO89/03883

PCT Pub. Date: May 5, 1989

Related U.S. Application Data

[63] Continuation-in-part of Ser. No. 151,526, Feb. 2, 1988, abandoned, and Ser. No. 113,014, Oct. 23, 1987, abandoned.

[51] Int. Cl.$^5$ .................. C12P 21/02; C12P 1/00; C12N 15/31; C12N 15/67
[52] U.S. Cl. .................. 435/69.1; 435/41; 435/69.6; 435/91; 435/172.3; 435/252.33; 435/320.1; 435/802; 435/804; 435/813; 435/818; 536/27; 935/11; 935/34; 935/38; 935/61; 935/67; 935/73
[58] Field of Search .................. 435/172.3, 253, 68, 435/240 Z, 69.1, 91, 252.33, 320.1, 41, 69.6; 536/27; 935/11, 34, 38, 61, 69, 73, 12, 29; 530/385

[56] References Cited

U.S. PATENT DOCUMENTS 4,615,974 10/1986 Kingsman et al. ................ 435/68
4,725,535 2/1988 Sonenshein et al. ................ 435/6
4,766,068 8/1988 Oeda et al. ................ 935/37 X

FOREIGN PATENT DOCUMENTS 8404538 11/1984 PCT Int'l Appl.

OTHER PUBLICATIONS

Ellis, J. G., et al. 1987 EMBO Journal vol. 6, pp. 11–16.
von Bodman, S. B., et al. 1986, Proc. Nat. Acad. Sci. U.S.A. vol. 83, pp. 9443–9447.
Unger, B. P. et al., 1986, J. Biol. Chem. vol. 261 pp. 1158–1163.
Zinoni, F., et al., 1986 Proc. Nat. Acad. Sci. U.S.A. vol. 83, pp. 4650–4654.
Rosenberg et al., Ann Rev. Genetics 13 319-23 (1979).
Nishi et al., Agric. Biol. Chem. 48(3), 669–75 (1984).
Wakabayashi et al., Nature vol. 322, 481-4 1986.
Stargaard et al., EMBO Journal vol. 6 3565–3569 (1987).
de Boer et al, Proc. Natl. Acad. Sci. vol. 80 pp. 21–25 (1983).
Boerman et al, J. Gen. App. Microbiol. 28 35-43 (1982).
Sato et al, Plasmid 6, 325 (1981).

Primary Examiner—Richard A. Schwartz
Assistant Examiner—Mary E. Mosher
Attorney, Agent, or Firm—Carolyn J. Adler; David W. Collins; Reginald J. Suyat

[57] ABSTRACT

The invention relates to nucleotide sequences, including a substantially purified gene which codes for an oxygen-binding protein, and a gene promoter/regulator which is useful in subjecting the translation/transcription of DNA sequences to selective regulation by external control, and plasmid vectors containing those nucleotide sequences, which are valuable bioprocessing catalysts for enhancing the growth characteristics of cells, and increasing production of various proteins and metabolites of those cells. Methods for the use of these nucleotide sequences and related plasmids for a range of applications including oxygen supply to cells, growth enhancement, expression of various gene products, enhancement of oxygen-requiring processes, binding and separation of oxygen from liquids and gases, and a range of oxidative reactions are also disclosed.

31 Claims, 1 Drawing Sheet

ENHANCEMENT OF CELL GROWTH BY EXPRESSION OF A CLONED HEMOGLOBIN GENE

The United States Government has certain rights in this invention.

CROSS-REFERENCE TO RELATED APPLICATIONS

The present application is a continuation-in-part application of applications Ser. No. 07/113,014, filed Oct. 23, 1987, now abandoned, and Ser. No. 07/151,526, filed Feb. 2, 1988, now abandoned.

TECHNICAL FIELD

This invention relates to the production of oxygen-binding proteins, particularly hemoglobins, and to enhancement of the growth and product synthesis characteristics of aerobic organisms in environments with sufficient as well as reduced or low levels of oxygen.

This invention relates generally to the use of recombinant DNA technology to direct or otherwise control gene expression in cultured cells, and more particularly, to methods and materials useful in subjecting the transcription and translation of DNA sequences to selective regulation by external control.

BACKGROUND ART

Globins such as hemoglobin and myoglobin are heme-containing oxygen carriers. By reversibly binding to oxygen in the presence of high oxygen concentrations and releasing it in regions or at times of low concentrations, these proteins considerably enhance the oxygen uptake rate of multicellular organisms over that allowed by mere passive diffusion. In unicellular organisms it is generally believed that the oxygen uptake rate is principally limited by the rate of transfer of dissolved oxygen in the environment or growth medium to the exterior cell surface. However, closer examination of cell structure reveals several potential diffusional barriers between environmental oxygen and the cytochromes where the oxygen finally undergoes reaction. For example, in gram negative bacteria, where the cytochromes are attached to the inside of the plasma membrane, the diffusing oxygen needs to cross transport barriers such as the cell wall, the outer membrane, the periplasmic space and the inner membrane before accepting electrons from metabolic reactions. In unicellular eucaryotes, where oxidative phosphorylation takes place in the mitochondria, there are further diffusional resistances. Small neutral molecules like oxygen are assumed to passively diffuse across these barriers; however, these barriers make a non-trivial contribution to the overall resistance to mass transfer to the actual reaction site and thus could be of significance under oxygen-limited conditions.

Physiological effects on growth due to depletion in dissolved oxygen levels has been demonstrated in the case of several organisms, including *Escherichia coli, Saccharomyces cerevisiae,* Pseudomonas strains, and *Alcaligenes eutrophus.* In *E. coli* for example, which has a very high affinity cytochrome, changes in dissolved oxygen tension leads to differential regulation of terminal oxidases, resulting in a decrease in the number of protons expelled per NADH molecule oxidized during aerobic respiration and, consequently, a possible adverse change in the stoichiometry of ATP biosynthesis. (Kranz et al., *Journal of Bacteriology* 158:1191–1194, 1984; Ingraham et al., *Growth of the bacterial cell,* Sinauer Associates, Inc. 1983, p. 147, both specifically incorporated herein.)

In addition to the respiratory oxygen requirement of aerobic organisms, oxygen-binding proteins have other potential applications as well, including, for example, the enhancement of particular oxidative transformations such as steroid conversions, vinegar production, biological waste treatment or enzymatic degradations, and in some steps in brewing or making distilled and fermented foods and beverages.

The filamentous bacterium, Vitreoscilla, a member of the Beggiatoa family, is a strict aerobe that is found in oxygen-poor environments such as stagnant ponds and decaying vegetable matter. Growth of the bacterium under hypoxic conditions results in a several-fold induction of synthesis of a homodimeric soluble heme protein (subunit MW 15,775) (Boerman et al., *Control of heme content in Vitreoscilla by oxygen,* Journal of General Applied Microbiology 28:35–42, 1982) which has a remarkable spectral (Webster, et al., *Reduced nicotinamide adenine dinucleotide cytochrome o reductase associated with cytochrome o purified from Vitreoscilla,* Journal of Biological Chemistry 249:4257–4260, 1974), structural (Wakabayashi, et al., *Primary sequences of a dimeric bacterial hemoglobin from Vitreoscilla,* Nature 322:481–483, 1986), and kinetic (Orii, et al., *Photodissociation of oxygenated cytochrome o(s) (Vitreoscilla) and kinetic studies of reassociation,* Journal of Biological Chemistry 261:2978–2986, 1986) homology with eucaryotic hemoglobins, and which is probably a true bacterial hemoglobin.

This protein was previously thought to be a cytochrome o, and it has been suggested to function in oxygen storage. However, biochemical discrepancies (Webster, et al., *Oxygenated cytochrome o,* Journal of Biological Chemistry 252:1834–1836, 1977) as well as the subsequent discovery of the true membrane-bound cytochromes o and d (DeMaio, et al., *Spectral evidence for the existence of a second cytochrome o in whole cells of Vitreoscilla,* Journal of Biological Chemistry 258:13768–13771, 1983; Webster et al., Federation Proceeding 44:678, 1985) led to further investigations of its spectral properties (Choc et al., *Oxygenated intermediate and carbonyl species of cytochrome o (Vitreoscilla),* Journal of Biological Chemistry 257: 865–869, 1982; Orii et al., supra.) and the eventual determination of its probable amino acid sequences and partial homology with known hemoglobin sequences.

Although these articles disclose the conservation of most features characteristic of eucaryotic hemoglobins, and discuss, to some extent, the role or potential role it probably plays in oxygen utilization, none of these researchers had previously been able to isolate a portable DNA sequence capable of directing intracellular production of this bacterial hemoglobin or to create a recombinant-DNA method for its production. Additionally, there has been no published proof of any oxygen transport or other kinetic function for this protein in Vitreoscilla, or any suggestion in the literature of any benefit from the introduction of a bacterial hemoglobin in heterologous organisms. Moreover, there has been no suggestion that such an oxygen-binding protein would have a far-reaching range of applications.

Surprisingly, the present inventors have discovered a portable DNA sequence capable of directing the recombinant-DNA synthesis of a bacterial hemoglobin.

The hemoglobin of the present invention, prepared by the recombinant-DNA methods set forth herein, will enable increased research into the growth of organisms in oxygen-poor environments. In addition, the oxygen-binding proteins of the present invention are useful in enhancing oxygen supply to cells or in other oxygen-utilizing processes, and for binding and separating oxygen from other fluids or gases. Furthermore, the oxygen-binding proteins of this invention are capable of increasing production of cells, or of proteins or metabolites normally made by a cell, or of natural or unnatural metabolites and proteins expressed in a cell via genetic manipulation. The proteins of this invention are also useful as selective markers in recombinant-DNA work, and have applications as diverse as enhancing certain oxygen-requiring steps in fermentation, enzymatic degradation, toxic chemical waste treatment, brewing, and particular oxidative reactions and transformations.

This invention also relates to certain DNA sequences which usually precede a gene in a DNA polymer and which provide a site for initiation of the transcription of that gene into mRNA. These are referred to as "promoter" sequences. Other DNA or RNA sequences, also usually but not necessarily "upstream" of a structural gene, bind proteins that determine the frequency or rate of transcription and/or translation initiation. These other sequences, including attenuators, enhancers, operators and the like, are referred to as "regulator" sequences. Thus, sequences which operate to determine whether the transcription and eventual expression of a gene will take place are collectively referred to as "promoter/regulator" DNA sequences.

The promoter/regulator sequences of genes are susceptible to enormous structural and functional variation, and in general, serve to regulate gene transcription in response to chemical and, sometimes, physical environmental conditions in and around the cell. Several generalized models for the action of promoter/regulator operation in gene transcription have been proposed. One model utilizes a repressor gene and a regulator sequence or operator sequence near the promoter of another gene. According to this model, transcription of the repressor sequence results in expression of a repressor protein which selectively binds to the operator sequence to effectively preclude transcription of the selected gene. An environmental signal, such as the increased concentration of a chemical acted upon by the protein product of the gene in question, may operatively inactivate the repressor protein, blocking its ability to bind to the operator sequence in a way which would interrupt transcription of the gene. Increased concentrations of a substrate could be seen as operating to induce synthesis of the protein which catalyzes its breakdown.

Another generalized model of operation of promoter/regulator sequences in the regulation of gene transcription suggests formation of an initially inactive form of repressor protein by the repressor DNA sequence. Such inactive form could not bind to an operator DNA sequence and disrupt selected gene transcription until it is combined with some other substance present in the cell, such as a compound which is the product of a reaction catalyzed by the protein coded for by the selected gene. Increased concentrations of such a reaction product in the cell would thus operate to repress the potential overproduction of proteins responsible for the product's synthesis. In these examples, the regulator protein functions to inhibit transcription. Other regulatory proteins have been described which potentiate or activate transcription of specific DNA sequences. Thus, there can be both positive and negative control proteins and corresponding regulatory DNA sequences.

Regulation of gene expression can also occur at the level of translation. For example, a regulator molecule could bind to a particular site on the messenger RNA, thus inhibiting or blocking translation.

Much of the genetic engineering activity to date has been oriented toward stably incorporating foreign DNA into cells, to provide not only a source of multiple copies of selected genes, but the large scale transcription and expression of commercially significant gene products.

The lactose ("lac") promoter/operator systems have been commonly used, for they are very controllable through the mode of action of the operator. When the operator is repressed, the DNA dependent RNA polymerase is completely prevented from binding and initiating transcription, thus effectively blocking promoter operability. This system can be derepressed by induction following the addition of a known inducer, such as isopropyl-beta-D-thiogalactoside (IPTG). The inducer causes the repressor protein to fall away so the RNA polymerase can function.

Cells transformed with plasmids carrying the lac promoter/operator system can be permitted to grow up to maximal density while in the repressed state through the omission of an inducer, such as IPTG, from the media. When a high level of cell density is achieved, the system can be derepressed by addition of inducer. The promoter is then free to initiate transcription and thus obtain expression of the gene products at yields commensurate with the promoter strength. However, certain of these inducible promoter systems are relatively weak and commercial or research productions using such systems do not urge the cell to generate maximum output.

In response to the need for microbial expression vehicles capable of producing desired products in higher yield, the tryptophan ("trp") promoter/operator system has become widely used. This system is one of several known systems with at least three times the strength of the lac promoter. However, it has the disadvantage of less promote control. The trp promoter is not inducible in the way the lac promoter is, namely, the bound repressor is not removed by induction. Instead, the system operates on a sort of feedback loop as described above. A system was devised whereby the attenuator region of the trp promoter/operator system was removed, with the resultant transformed cells being grown in tryptophan-rich media. This provided sufficient tryptophan to essentially completely repress the operator so that cell growth could proceed uninhibited by premature expression of any desired foreign proteins. When the culture reached appropriate growth levels, no additional tryptophan was supplied, resulting in mild tryptophan limitation, and, accordingly, derepression of the promoter with resultant expression of the desired protein gene insert. In application, this system has several disadvantages. For example, it is necessary to maintain high levels of tryptophan in the growth media to completely repress the promoter, and to permit the medium to become completely exhausted of tryptophan following full growth of the culture.

A hybrid system has been developed from the tryptophan and lactose promoter, wherein both promoters can be repressed by the lac repressor and both can be derepressed with IPTG. See De Boer et al., *The tac promoter: A functional hybrid derived from the trp and lac promoters*, Proc. Natl. Acad. Sci. USA, 80: 21-25, 1983. This system shares a disadvantage with the two discussed above, namely the required introduction of additional agents to a normal growth medium.

Another regulator/promoter system commonly used for expression of cloned proteins in *E. coli* is based on the $P_L$ promoter system from phage lambda. See Bernard and Helsinki, Methods in Enzymology, 68:482-492, 1979; *Use of Lambda Phage Promoter $P_L$ to Promote Gene Expression In Hybrid Plasmid Cloning Vehicles*. Induction of this promoter requires increase of culture temperature from 30° C. to 42° C. This system has the disadvantages of suboptimal growth rates at 30° C. prior to induction and upsetting of cell metabolism by the temperature shift. Temperature shift effects on metabolism are discussed, for example, by Neidhart, et al., *The Genetics And Regulation Of Heat-Shock Proteins*, Annual Reviews of Genetics, 18:295-329, 1984.

There has been a need in the art for an economical, simple, highly controllable and efficient promoter/regulator system for subjecting the transcription of DNA sequences to selective regulation by external control at constant temperature. The present inventors have discovered such an expression system, which can switch from low to very high expression activity upon reduction of dissolved oxygen concentration in the medium. This reduction in dissolved oxygen level is easily implemented at high cell densities without the need for addition of any chemical to the growth medium to induce gene expression.

DISCLOSURE OF THE INVENTION

The present invention relates to oxygen-binding proteins, particulary hemoglobins, a recominant-DNA method of producing same, and to portable DNA sequences capable of directing intracellular production of these oxygen-binding proteins. The present invention also relates to vectors containing these portable DNA sequences.

One object of the present invention is to provide a bacterial hemoglobin protein, which can be produced in sufficient quantities and purities to provide economical pharmaceutical, laboratory or industrial compositions which possess oxygen-binding activity.

An additional object of the present invention is to provide a recombinant-DNA method for the production of these oxygen-binding proteins. To facilitate the recombinant-DNA synthesis of these oxygen-binding proteins, it is a further object of the present invention to provide portable DNA sequences capable of directing intracellular production of oxygen-binding proteins. It is also an object of the present invention to provide cloning vectors containing these portable sequences. These vectors are capable of being used in recombinant systems to enhance the growth characteristics of organisms, and to produce useful quantities of oxygen-binding proteins. Augmented by intracellular synthesis of oxygen-binding proteins, product formation may also be enhanced.

The present invention also provides novel methods and materials for subjecting DNA sequences of living microorganisms to external regulation which is dependent upon availability of oxygen in the environment. Particularly, it relates to promoter/regulators, a recombinant-DNA method of producing same, and to portable DNA sequences capable of directing the translation and transcription initiation and control of the expression of desired gene products.

Thus, another object of the present invention is to provide for the control of expression of any selected chromosomal or extrachromosomal gene or DNA sequence through the incorporation of a promoter/regulator DNA sequence which is functionally responsive to environmental variations in the concentration of oxygen. The invention is thus broadly applicable to a variety of aerobic or slightly aerobic procedures for controlling genetic processes, ranging from the alteration of existing regulation of endogenous genes in prokaryotic and eucaryotic cells to securing selective, differential regulation of expression of selected exogenous or foreign genes stably incorporated in host cells.

Still another object of the present invention is to provide a promoter/regulator as described above, which can be produced in sufficient quantities and purities to provide their economical pharmaceutical, laboratory or industrial use.

An additional object of the present invention is to provide a recombinant-DNA method for the production of these promoter/regulators. To facilitate the recombinant-DNA synthesis of these promoter/regulators, it is a further object of the present invention to provide portable DNA sequences capable of controlling expression of gene products.

It is also an object of the present invention to provide cloning vectors containing these portable sequences. These vectors are capable of being used in recombinant systems to provide useful tools in the transformation of a wide variety of recipient cells.

Additional objects and advantages of the invention will be set forth in part in the description which follows, and in part will be obvious from the description or may be learned from practice of the invention. The objects and advantages may be realized and attained by means of the instrumentalities and combination particularly pointed out in the appended claims.

To achieve the objects and in accordance with the purposes of the present invention, oxygen-binding proteins are set forth which are capable of stoichiometric reaction with oxygen. To further achieve the objects and in accordance with the purposes of the present invention, as embodied and broadly described herein, portable DNA sequences coding for hemoglobin proteins are provided. Particularly, portable sequences are provided which code for the hemoglobin of the filamentous bacterium Vitreoscilla. These sequences comprise nucleotide sequences capable of directing intracellular production of oxygen-binding proteins. The portable sequences may by either synthetic sequences or restriction fragments ("natural" DNA sequences).

To achieve the objects and in accordance with the purposes of the present invention, promoter/regulators are also set forth. To further achieve the objects and in accordance with the purposes of the present invention, as embodied and broadly described herein, portable DNA sequences for these promoter/regulators are provided. Particularly preferred promoter/regulator DNA sequences for use in the practice of the present invention are derived from the filamentous bacterium Vitreoscilla. Portable nucleotide sequences are provided for these promoter/regulators. The portable sequences may be either synthetic sequences or restriction fragments ("natural" DNA sequences).

To facilitate identification and isolation of natural DNA sequences for use in the present invention, the inventors have developed a Vitreoscilla genomic library. This library contains the genetic information capable of directing a cell to synthesize the hemoglobin of the present invention. Other natural DNA sequences which may be used in the recombinant DNA methods set forth herein may be isolated from other genomic libraries.

Additionally, portable DNA sequences useful in the processes of the present invention may be synthetically created. These synthetic DNA sequences may be prepared by polynucleotide synthesis and sequencing techniques known to those of ordinary skill in the art.

Additionally, to achieve the objects and in accordance with the purposes of the present invention, a recombinant-DNA method is disclosed which results in manufacture by a host cell or microorganism of the instant oxygen-binding proteins using the portable DNA sequences referred to above. This recombinant-DNA method comprises:

(a) preparing a portable DNA sequence capable of directing a host cell to produce a protein having oxygen-binding activity, including hemoglobin activity;

(b) cloning the portable DNA sequence directly into a host cell, or into a vector capable of being transferred into and replicating in a host cell, such vector containing operational elements for the portable DNA sequence;

(c) transferring the vector, if one is used, containing the portable DNA sequence and operational elements into a host cell capable of expressing the oxygen-binding protein; and (d) culturing the host cell under conditions appropriate for replication and propagation of the vector and expression of the protein; and (e) in either order:
 (i) harvesting the protein; and
 (ii) permitting the protein to assume an active structure whereby it possesses oxygen-binding activity.

Additionally, to achieve the objects and in accordance with the purposes of the present invention, recombinant-DNA methods are disclosed which subject to external control the translation and transcription of gene products by a host cell or microorganism using the portable DNA sequences referred to above.

Processes of the invention include methods for subjecting the expression of a selected DNA sequence in a living cell or virus to regulation by oxygen level through the site-specific insertion of promoter/regulator DNA sequences responsive thereto. Also disclosed are improvements in prior methods for securing expression of a selected "foreign" or exogenous sequence in a host microorganism wherein the DNA sequence is stably incorporated as chromosomal or extrachromosomal constituent of the host. Such improvements comprise fusing to the selected DNA sequence a promoter/regulator DNA sequence capable of selectively promoting or inhibiting expression of the selected DNA in response to variations in environmental concentration of oxygen.

To further accomplish the objects and in further accord with the purposes of the present invention, cloning vectors are provided comprising at least one portable DNA sequence. In particular, plasmid pUC19/pRED2 is disclosed.

It is understood that both the foregoing general description and the following detailed description are exemplary and explanatory only and are not restrictive of the invention, as claimed.

The accompanying drawing, which is incorporated in and constitutes a part of this specification, illustrates one embodiment of the invention and, together with the description, serves to explain the principles of the invention.

BEST MODES FOR CARRYING OUT THE INVENTION

Figure 1:
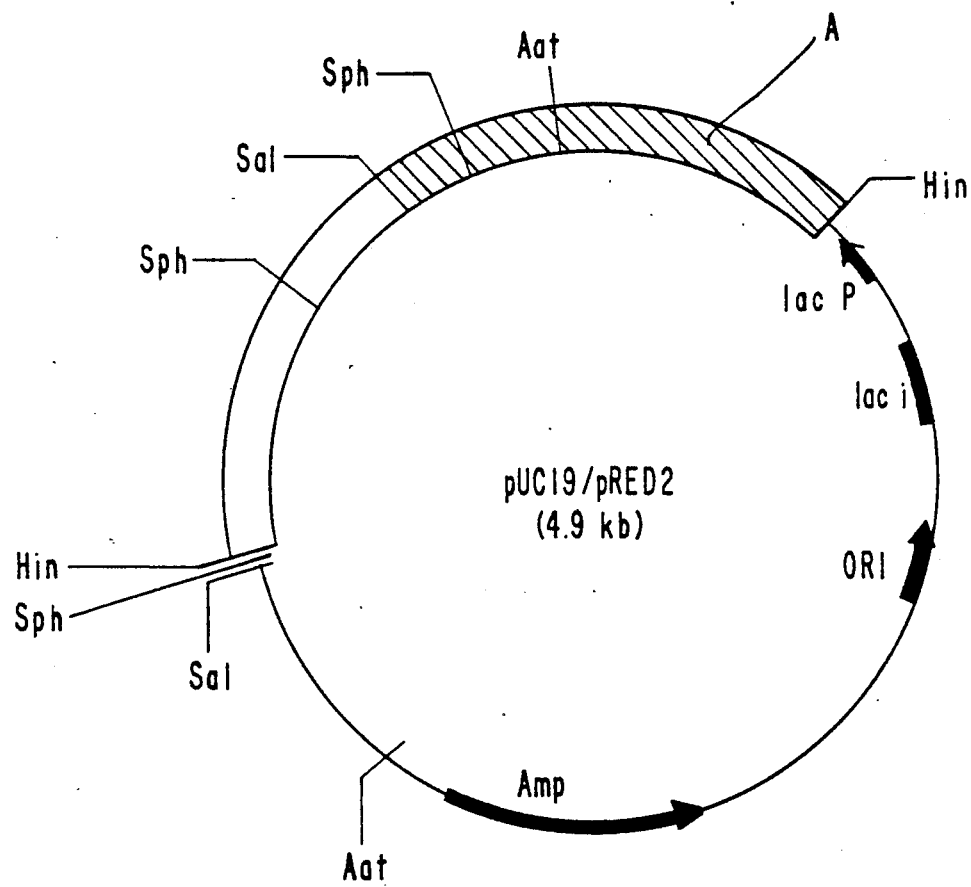
FIG. 1 is a partial restriction map of the plasmid pUC19/pRED2.

Reference will now be made in detail to the presently preferred embodiments of the invention, which, together with the drawing and the following examples, serve to explain the principles of the invention.

It must be understood that the present inventors have prepared an oxygen-binding protein and its natural promoter/regulator by recombinant DNA methods. While some methods for the production and use of these recombinant products are described below, the end use of these products alone is within the scope of the present invention.

As noted above, the present invention relates in part to portable DNA sequences capable of directing intracellular production of oxygen-binding proteins in a variety of host cells and host microorganisms. "Portable DNA sequence" in this context is intended to refer either to a synthetically produced nucleotide sequence or to a restriction fragment of a naturally occurring DNA sequence. For purposes of this specification, "oxygen-binding protein" is intended to mean a protein with a primary structure as defined by the codons present in the deoxyribonucleic acid sequence which directs intracellular production of the amino acid sequence, and which may or may not include post-translational modifications. It is contemplated that such post-translational modifications include, for example, association with a heme prosthetic group. It is further intended that the term "oxygen-binding protein" refers to either the form of the protein as would be excreted from a cell or as it may be present in the cell from which it was not excreted.

In a preferred embodiment, the portable DNA sequences are capable of directing intracellular production of hemoglobin. In a particularly preferred embodiment, the portable DNA sequences are capable of directing intracellular production of a hemoglobin biologically equivalent to that previously isolated from the filamentous bacterium, Vitreoscilla. By "biologically equivalent", as used herein, it is meant that a protein, produced using a portable DNA sequence of the present invention, is capable of binding oxygen in the same fashion, but not necessarily to the same degree, as the homodimeric soluble heme protein (subunit MW 15,775) isolable from Vitreoscilla.

As noted above, the present invention also relates in part to portable DNA sequences which contain promoter/regulators which are capable of directing intracellular expression of endogenous or exogenous gene products, in a variety of host cells and host microorganisms. "Portable DNA sequence" and "promoter/regulator" in this context are intended to refer either to a synthetically produced nucleotide sequence or to a restriction fragment of a naturally occurring DNA sequence.

The portable DNA sequences of the present invention may also include DNA sequences downstream from a promoter/regulator which code for at least one foreign protein. For purposes of this specification, "foreign protein" is intended to mean a protein with a primary structure as defined by the codons present in the deoxyribonucleic acid sequence which directs intracellular production of the corresponding amino acid sequence, and which may or may not include post-translational modifications. It is further intended that the term "foreign protein" refers to either the form of the protein as it would be excreted from a cell or as it may be present in the cell from which it was not excreted.

While the precise mechanism of regulation is not certain, the promoter/regulator is capable of directing intracellular production of hemoglobin and/or other operatively fused gene products upon a drop in oxygen available to the host cell.

In a particularly preferred embodiment, the promoter/regulator contains transcription and translation initiation and control sequences substantially equivalent to those for directing intracellular production of a hemoglobin protein biologically equivalent to that previously isolated from the filamentous bacterium, Vitreoscilla. By "substantially equivalent", as used herein, is meant that a promoter/regulator operates to express a downstream gene product upon reduction of the level of oxygen available to the host cell below some critical value.

It is of course intended that the promoter/regulators of the present invention may control and initiate transcription and translation of an unlimited number of endogenous and/or exogenous foreign proteins.

A first preferred portable DNA sequence for the promoter/regulators of the present invention contains at least a portion of the following nucleotide sequence, which reads 5' to 3' and includes the translation initiation sequence ATG (underlined) and some of the nucleotide sequence of the Vitreoscilla structural gene (also underlined):

with the underlining showing the homology in the above sequence to the consensus sequence, the $-10$ consensus sequence or Pribnow box sequence is TA TAAT(A/G). The $-35$ consensus sequence is TTGACA, and the consensus Shine-Dalgarno sequence is AGGAGGTXXX(XX)ATG.

In a preferred embodiment, the above sequence is operatively fused with at least a portion of a downstream sequence of nucleotides which code for at least a portion of the Vitreoscilla hemoglobin protein which contains at least a portion of the following amino acid sequence:

```
                5                          10
Met—Leu—Asp—Gln—Gln—Thr—Ile—Asn—Ile—Ile—
               15                          20
Lys—Ala—Thr—Val—Pro—Val—Leu—Lys—Glu—His—
               25                          30
Gly—Val—Thr—Ile—Thr—Thr—Thr—Phe—Tyr—Lys—
               35                          40
Asn—Leu—Phe—Ala—Lys—His—Pro—Glu—Val—Arg—
               45                          50
Pro—Leu—Phe—Asp—Met—Gly—Arg—Gln—Glu—Ser—
               55                          60
Leu—Glu—Gln—Pro—Lys—Ala—Leu—Ala—Met—Thr—
               65                          70
Val—Leu—Ala—Ala—Ala—Gln—Asn—Ile—Glu—Asn—
               75                          80
Leu—Pro—Ala—Ile—Leu—Pro—Ala—Val—Lys—Lys—
               85                          90
Ile—Ala—Val—Lys—His—Cys—Gln—Ala—Gly—Val—
               95                         100
Ala—Ala—Ala—His—Tyr—Pro—Ile—Val—Gly—Gln—
              105                         110
Glu—Leu—Leu—Gly—Ala—Ile—Lys—Glu—Val—Leu—
```

Hin:

AAGCTTAACG GACGCTGGGG TTAAAAGTAT TTGAGTTTTG ATGTGGATTA AGTTTTAAGA 60

GGCAATAAAG ATTATAATAA GTGCTGCTAC ACCATACTGA TGTATGGCAA AACCATAATA 120

ATGAACTTAA GGAAGACCCT CATGTTAGAC CAGCAAACCA TTAACATCAT CAAAGCCACT 180

GTTCCTGTAT TGAAGGAGCA TGGCGTTACC ATTACCACGA CTTTTTATAA AAACTTGTTT 240

GCCAAACACC CTGAAGTACG TCCTTTGTTT GATATGGGTC GCCAAGAATC TTTGGAGCAG 300

CCTAAGGCTT TGGCGATGAC GGTATTGGCG GCAGCGCAAA ACATTGAAAA TTTGCCAGCT 360

ATTTTGCCTG CGGTCAAAAA AATTGCAGTC AAACATTGTC AAGCAGGCGT GGCAGCAGCG 420

CATTATCCGA TTGTCGGTCA AGAATTGTTG GGTGCGATTA AAGAAGTATT GGGCGATGCC 480

GCAACCGATG ACATTTTGGA CGCGTGGGGC AAGGCTTATG GCGTGATTGC AGATGTGTTT 540

ATTCAAGTGG AAGCAGATTT GTACGCTCAA GCGGTTGAAT AAAGTTTCAG GCCGCTTTCA 600

GGACATAAAA AACGCACCAT AAGGTGGTCT TTTTACGTCT GATATTTACA CAGCAGCAGT 660

TTGGCTGTTG GCCAAAACTT GGGACAAATA TTGCCCTGTG TAAGAGCCCG CCGTTGCTGC 720

GACGTCTTCA GGTGTGCCTT GGCAT 745

The nucleotide bases represented by the above abbreviations are as follows: A=Adenine, G=Guanine, C=Cytosine, and T=Thymine.

The above sequence exhibits homology with certain sequences which are highly conserved in a variety of promoter/regulators. Using conventional numbering, -continued

```
              115                    120
Gly—Asp—Ala—Ala—Thr—Asp—Asp—Ile—Leu—Asp—

125                    130
Ala—Trp—Gly—Lys—Ala—Tyr—Gly—Val—Ile—Ala—

135                    140
Asp—Val—Phe—Ile—Gln—Val—Glu—Ala—Asp—Leu—

145                    150
Tyr—Ala—Gln—Ala—Val—Glu
```

This amino acid sequence is disclosed in Wakabayashi et al., supra, *Nature* 322:483, 1986. It is presently believed that the protein purified and prepared through the practice of this invention will exhibit a homology of over 80% with this sequence. The protein of this invention has been observed to enhance functioning of a cell in low oxygen environments (Khosla and Bailey, unpublished results).

The amino acids represented by the foregoing abbreviations are as follows:

| Amino Acid | 3-Letter Symbol |
|---|---|
| Glycine | Gly |
| Alanine | Ala |
| Valine | Val |
| Leucine | Leu |
| Isoleucine | Ile |
| Arginine | Arg |
| Lysine | Lys |
| Glutamic acid | Glu |
| Aspartic acid | Asp |
| Glutamine | Gln |
| Asparagine | Asn |
| Threonine | Thr |
| Serine | Ser |
| Cysteine | Cys |
| Methionine | Met |
| Phenylalanine | Phe |
| Tyrosine | Tyr |
| Tryptophan | Trp |
| Proline | Pro |
| Histidine | His |

It must be borne in mind in the practice of the present invention that the alteration of some amino acids in a protein sequence may not affect the fundamental properties of the protein. Therefore, it is also contemplated that other portable DNA sequences, both those capable of directing intracellular production of identical amino acid sequences and those capable of directing intracellular production of analogous amino acid sequences which also possess oxygen-binding activity, are included within the ambit of the present invention.

It must also be borne in mind in the practice of the present invention that the alteration of some nucleotide bases in a DNA sequence may not affect the fundamental properties of the coding sequence. Therefore, it is also contemplated that other analogous portable DNA promoter/regulator sequences which are operable through changes in oxygen level are included within the ambit of the present invention.

It is contemplated that some of these analogous amino acid sequences will be substantially homologous to native Vitreoscilla hemoglobin while other amino acid sequences, capable of functioning as oxygen-binding proteins, will not exhibit substantial homology to native Vitreoscilla hemoglobin. By "substantial homology" as used herein, is meant a degree of homology to native Vitreoscilla hemoglobin in excess of 50%, preferably in excess of 80%.

Similarly, it is contemplated that some of these analogous DNA sequences will be substantially homologous to the sequence set forth above, while other DNA sequences, capable of functioning as the promoter/regulator described above, will not exhibit substantial homology to the sequence outlined above.

As noted above, the portable DNA sequences of the present invention may be synthetically created, by hand or with automated apparatus. It is believed that the means for synthetic creation of these polynucleotide sequences are generally known to one of ordinary skill in the art, particularly in light of the teachings contained herein. As examples of the current state of the art relating to polynucleotide synthesis, one is directed to Maniatis et al., *Molecular Cloning—A Laboratory Manual,* Cold Spring Harbor Laboratory (1984), and Horvath et al. *An Automated DNA Synthesizer Employing Deoxynucleoside 3'-Phosphoramidites,* Methods in Enzymology 154:313-326, 1987, hereby incorporated by reference.

Additionally, the portable DNA sequence may be a fragment of a natural sequence, i.e., a fragment of a polynucleotide which occurred in nature and which has been cloned and expressed for the first time by the present inventors. In one embodiment, the portable DNA sequence is a restriction fragment isolated from a genomic library. In this preferred embodiment, the genomic library is created from the bacterium Vitreoscilla. In other alternative embodiments, the portable DNA sequence is isolated from other genomic and cDNA libraries.

While it is envisioned that the portable DNA sequences of this invention ma desirably be inserted directly into the host chromosome, the present invention also provides a series of vectors, each containing at least one of the portable DNA sequences described herein. It is contemplated that additional copies of the portable DNA sequence may be included in a single vector to increase a host cell's ability to produce large quantities of the desired oxygen-binding protein. It is also envisioned that other desirable DNA sequences may also be included in the vectors of this invention. Further, the invention may be practiced through the use of multiple vectors, with additional copies of at least one of the portable DNA sequences of this invention and perhaps other desirable DNA sequences.

In addition, the cloning vectors within the scope of the present invention may contain supplemental nucleotide sequences preceding or subsequent to the portable promoter/regulator and/or DNA sequence. These supplemental sequences are those that will not adversely interfere with transcription of the portable promoter/regulator and/or any fused DNA sequence and will, in some instances, enhance transcription, translation, post-translational processing, or the ability of the primary amino acid structure of the resultant gene product to assume an active form.

A preferred vector of the present invention is set forth in FIG. 1. This vector, pUC19/pRED2, contains the preferred nucleotide sequence which codes for the amino acids set forth above. Vector pUC19/pRED2 cells are on deposit in the American Type Culture Collection ("ATCC") in Rockville, Md. under Accession No. 67536.

A preferred nucleotide sequence encoding the Vitreoscilla hemoglobin protein and adjacent Vitreoscilla sequences described above is identified in FIG. 1 as region A. The above nucleotide sequence reads counterclockwise through region A of FIG. 1. Plasmid pUC19/pRED2 may also contain supplemental nucleotide sequences preceding and subsequent to the preferred DNA sequence in region A, such as terminators, enhancers, attenuators and the like. For proteins to be exported from the intracellular space, at least one leader sequence and any other DNA sequences necessary or preferred for appropriate transcription and subsequent translation of the vector DNA may be included within the scope of this invention.

In a preferred embodiment, cloning vectors containing and capable of expressing the portable DNA sequence of the present invention contain various operational elements in addition to or instead of the promoter/regulator disclosed and claimed herein. These "operational elements" may include at least one promoter, at least one sequence that acts as expression regulator, and at least one terminator codon, at least one leader sequence, and any other DNA sequences necessary or preferred for appropriate transcription and subsequent translation of the vector DNA.

Additional embodiments of the present invention are envisioned as employing other known or currently undiscovered vectors which would contain one or more of the portable DNA sequences described herein. In particular, it is preferred that these vectors have some or all of the following characteristics: (1) possess a minimal number of host-organism sequences; (2) be stable in the desired host; (3) be capable of being present in a high copy number in the desired host; (4) possess a regulatable promoter; and (5) have at least one DNA sequence coding for a selectable trait present on a portion of the plasmid separate from that where the portable DNA sequence will be inserted. Alteration of vectors to meet the above criteria are easily performed by those of ordinary skill in the art in light of the available literature and the teachings herein. It is to be understood that additional cloning vectors may now exist or will be discovered which have the above-identified properties and are therefore suitable for use in the present invention and these vectors are also contemplated as being within the scope of this invention.

As set forth in Example I, an *E. coli* vector system is a preferred embodiment. Various cloning vehicles are required for the range of host cells and organisms suitable for insertion of the portable DNA sequences of the present invention, as set forth below. In light of the available literature, choice of such a cloning vehicle, if necessary, is within the ordinary skill in the art.

Additional bacterial hosts are suitable, including, without limitation: bacteria such as members of the genera Bacillus, Pseudomonas, Alcaligenes, Streptococcus, Lactobacillus, Methylophilus, Xanthomonas, Corynebacterium, Brevibacterium, Acetobacter, and *Streptomyces*.

Examples of suitable eucaryotic host microorganisms would include fungi, yeasts such as Saccharomyces and Candida, and molds such as Aspergillus, Pennicillim and Cephalosporium.

It is envisioned that the scope of this invention would cover expression systems in eucaryotic microorganisms and host cultured cells derived from multicellular organisms, including animals, insects and plants, which are grown in the presence of oxygen. The promoter/regulator of the present invention is especially useful in a host which switches from low to very high expression activity upon reduction of dissolved oxygen concentration in the medium. Such expression systems need not be derived from Vitreoscilla.

Various vector systems will be suitable for these and other desirable hosts, including plasmids, viruses and bacteriophages. The following, noninclusive list of cloning vectors is believed to set forth vectors which can easily be altered to meet the above criteria and are therefore preferred for use in the present invention. Such alterations are easily performed by those of ordinary skill in the art in light of the available literature and the teaching herein.

For example, many selectable cloning vectors have been characterized for use in *E. coli*, including pUC8, pUC9, pBR322, pGW7, placI$^q$, and pDP8, Maniatis et al., supra. A bifunctional vector that replicates in *E. coli* and can also be used in Streptomyces is pKC462a. Suitable vectors for use in Bacillus include: pUB110, pSA0501, pSA2100, pBD6, pBD8, and pT127, Ganesan and Hock, eds., *Genetics and Biotechnology of Bacilli*, Academic Press 1984. In Pseudomonas, RSF1010, Pms149, pKT209, and RK2 are suitable; some of these vectors are useful in a wide range of gram-negative bacteria including Agrobacterium and Xanthomonas. For Saccharomyces, it is possible to use YEp24, YIp5, and YRp17, Botstein and Davis, *Molecular Biology of the Yeast Saccharomyces* (Strathern et al., eds), Cold Spring Harbor Laboratory, 1982. In mammalian systems retrovirus vectors such as those derived from SV40 are typically used.

Synthesis and/or isolation of necessary and desired component parts of cloning vectors, and their assembly is believed to be within the duties and tasks performed by those with ordinary skill in the art and, as such, are capable of being performed without undue experimentation.

In construction of the cloning vectors of the present invention, it should additionally be noted that multiple copies of the promoter/regulator with any fused gene sequences and/or of the portable DNA sequence coding for the oxygen-binding protein and its attendant operational elements as necessary may be inserted into each vector. In such an embodiment, the host organism would produce greater amounts per vector of the desired oxygen-binding protein. The number of multiple copies of the DNA sequence which may be inserted into the vector is limited only by the ability of the resultant vector, due to its size, to be transferred into and replicated and expressed in an appropriate host.

Additionally, it is preferred that the cloning vector contain a selectable marker, such as a drug resistance marker or other marker which causes expression of a selectable trait by the host. In a particularly preferred embodiment of the present invention, the gene for ampicillin resistance is included in vector pUC19/pRED2. Such a drug resistance or other selectable marker is intended in part to facilitate in the selection of transformants. Additionally, the presence of such a selectable marker on the cloning vector may be of use in keeping contaminating microorganisms from multiplying in the culture medium. In this embodiment, such a pure culture of the transformed host organisms would be obtained by culturing the organisms under conditions which require the induced phenotype for survival.

It is noted that the portable DNA sequence of the present invention may themselves be used as a selectable marker, in that they provide enhanced growth characteristics in low oxygen circumstances, and also engender an easily visible reddish tint in the host cells.

The promoter/regulators of this invention are capable of controlling expression of proteins or, thereby, of controlling synthesis of metabolites normally made by a cell, or of natural or unnatural metabolites and proteins expressed in a cell via genetic manipulation. This would include heterologous proteins—either intracellular or extracellular—as well as biopolymers such as polysaccharide materials, simpler metabolites such as amino acids and nucleotides, antibiotics and other chemicals produced by living cells or cellular biocatalysts.

The oxygen-binding proteins of the present invention, prepared by the recombinant-DNA methods set forth herein, will enable increased research into the growth of organisms in oxygen-poor environments. In addition, the oxygen-binding proteins of the present invention are useful in enhancing oxygen supply to cells or in other oxygen-utilizing processes (Adlercreutz et al., *Biocatalyst in Organic Synthesis*, Symposium of the Working Party on Immobilized Biocatalysts of the European Federation of Biotechnology, Abstracts, p. 18, 1985), and for binding and separating oxygen from other fluids or gases (Bonaventura et al., *Underwater Life Support Based on Immobilized Oxygen Carriers*, Applied Biochemistry and Biotechnology 9:65-80, 1984). Furthermore, the oxygen-binding proteins of this invention are capable of increasing production of cells, or of proteins or metabolites normally made by a cell, or of natural or unnatural metabolites and proteins expressed in a cell via genetic manipulation. This would, as described above, include heterologous proteins, biopolymers, simpler metabolites, antibiotics, and other chemicals produced by living cells or cellular biocatalysts.

The protein products of this invention also have applications as diverse as enhancing certain oxygen-requiring steps in fermentation, enzymatic degradation, toxic chemical waste treatment, brewing and particular oxidative reactions and transformations such as steroid conversions.

This invention also relates to a recombinant-DNA method for the production of oxygen-binding proteins. Generally, this method includes:

(a) preparing a portable DNA sequence capable of directing a host cell or microorganism to produce a protein having oxygen-binding activity;

(b) transferring the portable DNA sequence directly into the host, or cloning the portable DNA sequence into a vector capable of being transferred into and replicating in a host cell or microorganism, such vector containing operational elements for the portable DNA sequence;

(c) transferring the vector containing the portable DNA sequence and operational elements into a host cell or microorganism capable of expressing the oxygen-binding protein;

(d) culturing the host microorganism under conditions appropriate for replication and propagation of the vector and/or expression of the protein; and (e) in either order:

(i) harvesting protein; and (ii) permitting the protein to assume an active structure whereby it possesses oxygen-binding activity.

In this method, the portable DNA sequences are those synthetic or naturally-occurring polynucleotides described above. In a preferred embodiment, the portable DNA sequence codes for at least a portion of the Vitreoscilla hemoglobin protein described above.

This invention also relates to a recombinant-DNA method for the use of these promoter/regulators. Generally, this method provides a process for subjecting the expression of a selected DNA sequence to external control under given environmental conditions which comprises the steps of:

(a) providing at least one selected isolated structural gene that is transcriptionally and/or translationally responsive to a Vitreoscilla hemoglobin promoter/regulator DNA sequence under the given environmental conditions; and (b) operatively fusing the selected structural gene with said promoter/regulator DNA sequence.

It is envisioned that the portable DNA sequences may be inserted directly into the host chromosome, or alternatively may utilize a vector cloning system. The vectors contemplated as being useful in the present method are those described above. In a preferred embodiment, the cloning vector pUC19/pRED2 is used in the disclosed method.

A vector thus obtained may then be transferred into the appropriate host cell or organism. It is believed that any microorganism having the ability to take up exogenous DNA and express those genes and attendant operational elements may be chosen. Particular hosts which may be preferable for use in this invention include those described above. Methods for transfer of vectors into hosts are within the ordinary skill in the art. For ultimate expression in certain microorganisms such as yeast, it may desirable that the cloning vector be first transferred into another microorganism such as *Escherichia coli*, where the vector would be allowed to replicate and from which the vector would be obtained and purified after amplification, and then transferred into the yeast for ultimate expression of the oxygen-binding protein.

The host cells or microorganisms are cultured under conditions appropriate for the expression of the oxygen-binding protein. These conditions ar generally specific for the host organism, and are readily determined by one of ordinary skill in the art, in light of the published literature regarding the growth conditions for such organisms.

In one embodiment, conditions necessary for the regulation of the expression of the DNA sequence, dependent upon any operational elements inserted into or present in the vector, would be in effect at the transformation and culturing stages. The cells are grown to a high density in the presence of appropriate regulatory conditions which inhibit the expression of the DNA sequence. When optimal cell density is approached, the environmental conditions are altered to those appropriate for the expression of the portable DNA sequence. It is thus contemplated that the production of a cloned protein will occur in a time span subsequent to the growth of the host cells to near optimal density, and that the resultant cloned protein product would be harvested, if desired, at some time after the regulatory conditions necessary for its expression were induced.

Where the operational elements used are in the promoter/regulator sequence of this invention, these conditions are as follows. The cells are grown to a high density in the presence of appropriate levels of oxygen which inhibit the expression of the DNA sequence. When optimal cell density is approached, the environmental oxygen level is altered to a lower value appropriate for the expression of the portable DNA sequence. Levels from less than in a 1% oxygen-saturated solution to oxygen saturated are within the scope of this invention. It is thus contemplated that the production of any desired fused product will occur in a time span subsequent to the growth of the host cells to near optimal density, and that the resultant product would be harvested, if desired, at some time after the oxygen level necessary for its expression were reached.

If harvesting of the oxygen-binding protein products of the present invention is desired, it may be done prior or subsequent to purification and prior or subsequent to assumption of an active structure.

It is currently believed that some percentage of the oxygen-binding proteins of the present invention will assume their proper, active structure upon expression in the host cell or organism. If desired, the oxygen-binding protein may be transported across a cell membrane. This will generally occur if DNA coding for an appropriate leader sequence has been linked to the DNA coding for the recombinant protein. The structures of numerous signal peptides have been published. It is envisioned that these leader sequences, included in or added to at least some portion of the portable DNA as necessary, will direct intracellular production of a fusion protein which will be transported through the cell membrane and will have the leader sequence cleaved upon release from the cell.

Additional uses of the oxygen-binding proteins of the present invention are envisioned. The purified proteins and/or the whole cells and/or extracts of the cells of the present invention themselves may be used to bind to oxygen or proteins and thus could function somewhat as erythrocytes.

The present invention may also be used as a method for transporting and enhancing oxygen supply to cells or in other oxygen-utilizing processes by delivering the oxygen-binding proteins—isolated in lysates and crude cell preparations, purified from extracts, in synthetic sequences, or in whole cells containing the proteins—where desired. It is envisioned that the protein products of the present invention could valuably be added to media for culturing cells and thereby enhance the transport of oxygen.

It is also envisioned that the proteins of the present invention may be used for binding and separating of oxygen from fluids such as seawater and from other gases.

It is understood that application of the teachings of the present invention to a specific problem or environment will be within the capabilities of one having ordinary skill in the art in light of teachings contained herein. Examples of the products of the present invention and representative processes for their isolation, use and manufacture appear below.

INDUSTRIAL APPLICABILITY

The products and processes of the present invention find usefulness in a range of medical, laboratory and industrial applications. The invention provides metabolically engineered cells with enhanced growth characteristics for increasing production of various proteins or metabolites by those cells. The invention further provides a method for subjecting expression of a certain DNA sequence to external control under given environmental conditions. Also provided are recombinant-DNA fusion gene products, expression vectors, and nucleotide base sequences for the practice of the invention. The products and processes of the present invention find applications in a range of aerobic processes, such as manufacture of cloned proteins and synthesis of metabolites, chemical production by fermentation, enzymatic degradation, waste treatment, brewing and a range of oxidative reactions.

EXAMPLE 1

Cloning and Expression of Hemoglobin from Vitreoscilla in *Escherichia coli*

Materials and Methods

Vitreoscilla sp. (Murray strain no. 389) was obtained from Dr. Webster (Department of Biology, Illinois institute of Technology, Chicago, Ill. 60616, U.S.A.), and grown in a medium containing 1.5% yeast extract, 1.5% peptone, and 0.02% sodium acetate (pH 8.0 with NaOH).

*E. coli* JM101 were obtained from the laboratory of Dr. Simon (Division of Biology, California Institute of Technology, Pasadena, Calif. 91125, U.S.A.), and grown in L broth containing 1% Bactotryptone, 0.5% yeast extract and 1% sodium chloride.

Plasmid pUC19 (Yanisch-Perron et al., *Improved M13 phage cloning vectors and host strains: nucleotide sequences of m13mp18 and pUC19 vectors*, Gene 33:103–109, 1985) packaging kits were purchased from Pharmacia. All restriction enzymes, T4 polyneucleotide kinase and T4 ligase were from New England Biolabs or Bethesda Research Laboratories. Calf intestine alkaline phosphatase was from Pharmacia. Mixed oligonucleotide probes were synthesized with an Applied Biosystems synthesizer. Kodak XAR5 x-ray film was used for autoradiography. Geneclean kits were purchased from Bio101. All other chemicals were of analytical grade.

Vitreoscilla genomic DNA was isolated according to the protocol of Silhavy et al., *Experiments with gene fusions*, Cold Spring Harbor Laboratory (1984), specifically incorporated herein. HindIII-digested Vitreoscilla DNA was ligated into the phosphatased HindIII site of pUC19 and transformed into JM101. Recombinant colonies and plaques were transferred on nitrocellulose filters as described in Maniatis, et al., *Molecular cloning—a laboratory manual*, Cold Spring Harbor Laboratory (1982) and specifically incorporated herein. Rapid plasmid isolation from recombinant colonies were done according to Silhavy et al., supra. Digested fragments of plasmid DNA or fractions of genomic DNA were isolated from agarose gels using Geneclean kits. *E. coli* cells were transformed by the $CaCl_2$ method of Silhavy et al., supra. Plasmid uptake was induced by heat-shocking chilled competent cells at 37° C. for 5 minutes.

For Southern hybridizations the reagents suggested in Dupont catalog No. NEF-976, *Protocols for electrophoretic and capillary transfer of DNA and RNA, DNA and RNA hybridization, and DNA and RNA rehybridization* (1985), specifically incorporated herein, were used, whereas for colony and plaque hybridizations those described in Maniatis et al., supra, were used. Filters were prehybridized at 45°–50° C. for 2–4 hours and hybridized at 30° C. for 20–24 hours. 200 picomoles oligonucleotide kinased with 200 microCi ($^{32}P$)ATP (sp. act. 7000 Ci/mmol) were used as probe. Filters were washed in 2×SSC, 0.1% SDS at room temperature (3×5 minutes) and at 46° C. (for the C-terminal probe) and 50° C. (for the N-terminal probe) prior to autoradiography.

SDS-polyacrylamide gel electrophoresis was done according to standard protocols, Laemmli, *Cleavage of* structural proteins during the assembly of the head of bacteriophage T4, Nature 227:680–685, 1970, specifically incorporated herein, with a 12.5% resolving gel. Protein in the gel was visualized by the silver staining method of Merril et al., *Ultrasensitive strain for proteins in polyacrylamide gels shows regional variation in cerebrospinal fluid proteins*, Science 211:1437–1438, 1983.

Results

Three sets of mixed oligonucleotide probes were synthesized which had a predicted homology to two domains in the hemoglobin gene, one N-terminal and one C-terminal. A pUC19-HindIII library of Vitreoscilla DNA was test-plated on rich plates with ampicillin, X-gal and IPTG. More than 70% of the colonies were probable recombinants, as estimated by visual inspection. About 10,000 colonies were then screened. Three positives were identified. Because of the high density of colonies on the plate, these, along with their immediate clones from each group, were assayed by rapid isolation and HindIII digestion. One of these, pRED1, had three inserted fragments including a 2.2 kb one. Subsequent digestion of this plasmid with various endonucleases and Southern hybridization of the resulting DNA bands did confirm that the 2.2 kb band did indeed contain the entire hemoglobin gene, since no HindIII sites are expected to exist upstream or downstream of the regions spanned by the oligomeric probes.

The HindIII fragment from pRED1 that contained the hemoglobin structural gene was purified and reinserted by standard protocols into pUC19 in both orientations (pRED2 and pRED3). *E. coli* cells containing plasmids pRED1, pRED2, pRED3 and pUC19 as well as Vitreoscilla cells were grown to stationary phase and cell extracts were assayed on an SDS-polyacrylamide gel for the existence of the hemoglobin polypeptide. The hemoglobin was expressed as a major cellular protein in all recombinant cells. Since both plasmids pRED2 and pRED3 express about equal amounts of this polypeptide, it is presently believed that the gene is probably expressed from its natural promoter in *E. coli*.

The restriction map of plasmid pRED2 is shown in FIG. 1.

EXAMPLE 2

Complete Nucleotide Sequence

Determination of the sequence of the relevant region of the fragment isolated from the Vitreoscilla genomic library was accomplished as follows:

The HindIII-SphI fragment from plasmid pRED2 which contains the structural gene and adjacent sequences was subcloned into pUC19 (purchased from Bethesda Research Labs) to obtain plasmid pRED4. An MluI site was identified, by restriction mapping the resulting plasmid, which breaks up the HindIII-SphI insert into two fragments which were individually sequenced using conventional protocols (Maxam and Gilbert, *Sequencing end-labeled DNA with base-specific chemical cleavages*, Methods in Enzymology 65: 499–560, 1980; Iverson and Dervan, *Adenine specific DNA chemical sequencing reaction*, Nuclear Acids Research 15: 7823–7830, 1987).

The nucleotide sequence of the important portion of the HindIII-SphI fragment is as listed below. It includes a putative *E. coli* promoter, ribosome binding site, the complete VHb structural gene (start and stop codons are underlined) and a putative *E. coli* transcription terminator (Khosla and Bailey, *The Vitreoscilla hemoglobin gerne: molecular cloning, nucleotide sequence and genetic expression in Escherichia coli*, Mol. & Gen. Genet., in press).

```
AAGCTTAACG GACGCTGGGG TTAAAAGTAT TTGAGTTTTG ATGTGGATTA AGTTTTAAGA    60

GGCAATAAAG ATTATAATAA GTGCTGCTAC ACCATACTGA TGTATGGCAA AACCATAATA   120

ATGAACTTAA GGAAGACCCT CATGTTAGAC CAGCAAACCA TTAACATCAT CAAAGCCACT   180

GTTCCTGTAT TGAAGGAGCA TGGCGTTACC ATTACCACGA CTTTTTATAA AAACTTGTTT   240

GCCAAACACC CTGAAGTACG TCCTTTGTTT GATATGGGTC GCCAAGAATC TTTGGAGCAG   300

CCTAAGGCTT TGGCGATGAC GGTATTGGCG GCAGCGCAAA ACATTGAAAA TTTGCCAGCT   360

ATTTTGCCTG CGGTCAAAAA AATTGCAGTC AAACATTGTC AAGCAGGCGR GGCAGCAGCG   420

CATTATCCGA TTGTCGGTCA AGAATTGTTG GGTGCGATTA AAGAAGTATT GGGCGATGCC   480

GCAACCGATG ACATTTTGGA CGCGTGGGGC AAGGCTTATG GCGTGATTGC AGATGTGTTT   540

ATTCAAGTGG AAGCAGATTT GTACGCTCAA GCGGTTGAAT AAAGTTTCAG GCCGCTTTCA   600

GGACATAAAA AACGCACCAT AAGGTGGTCT TTTTACGTCT GATATTTACA CAGCAGCAGT   660

TTGGCTGTTG GCCAAAACTT GGGACAAATA TTGCCCTGTG TAAGAGCCCG CCGTTGCTGC   720

GACGTCTTCA GGTGTGCCTT GGCAT                                         745
```

EXAMPLE 3

Growth Enhancement in *E. coli* with pRED2: Shake Flask Cultures

In this Example, the growth behavior of *E. coli* cells producing active Vitreoscilla hemoglobin was compared to that of control strains grown under identical conditions. The following strains were studied: (1) JM101:pRED2; (2) JM101:pUC9; and (3) JM101. Plasmids pUC9 and pUC19 are essentially identical except for a different in one restriction site unrelated to the insert or to any of the functional properties of the plasmid.

Experimental Protocol

Cells were grown at 37° C. in a complex medium containing 1% (W/V) bactotryptone, 0.5% (W/V)

yeast extract, 0.5% (W/V) NaCl, 0.3% (W/V) $K_2HPO_4$ and 0.1% (W/V) $KH_2PO_4$ (pH 7.0). Plasmid-containing cells were grown in the presence of 100 mg/L ampicillin. In each case the shake-flask was inoculated with a 1% (V/V) dose of concentrated nutrient broth containing 430 g/L glucose, 5 g/L yeast extract, 110 g/L $(NH_4)_2SO_4$, 8 g/L $MgSO_4.7H_2O$, 0.27 g/L $FeCl_3.6H_2O$, 0.02 g/L $ZnCl_2.4H_2O$, 0.02 g/L $CaCl_2.2H_2O$, 0.02 g/L $NaMoO_4.2H_2O$, 0.01 g/L $CuSO_4.5H_2O$, 0.005 g/L $H_3BO_3$, 0.1% (V/V) conc. HCl, 4.2 mg/L riboflavin, 54 mg/L pantothenic acid, 60 mg/L folic acid. This formulation has been successfully used on a previous occasion to grow stationary cells to a high density in a fedbatch mode. The cells were then allowed to grow further until stationary phase was reached again. Optical density was measured at 600 nm on a Bausch & Lomb Spectronic 21 spectrophotometer. Dry weights were measured by spinning 10 mL samples at 4° C., washing once with distilled water and subsequently drying the resuspended sample at 100° C. overnight. The heme content of the cells was assayed according to the method of Lamba & Webster (Lamba & Webster, *Effect of growth conditions on yield and heme content of Vitreoscilla*. Journal of Bacteriology 142:169–173, 1980), and the hemoglobin activity was measured by the method of Webster & Liu (Webster and Liu, *Reduced nicotinamide adenine dinucleotide cytochrome o reductase associated with cytochromic o purified from Vitreoscilla*, Journal of Biological Chemistry, 249:4257–4260, 1974.).

Results

The growth properties, heme content and hemoglobin activity of the three strains are documented in the Table below.

|  | JM101:pRED2 | JM101:pUC9 | JM101 |
|---|---|---|---|
| 1. $OD_{600}$ before nutrient replenishment | 0.937 | 0.737 | 0.945 |
| 2. $OD_{600}$ | 1.230 | 0.880 | 0.985 |
| 3. max. attained dry wt. | 1.5 g/L | 0.85 g/L | 1 g/L |
| 4. relative heme content | 5.5 | 1 | ** |
| 5. relative hemoglobin activity | 5 | 1 | ** |
| 6. specific growth rate* | 0.04/h | 0.01/h | 0.009/h |

*mean value following additional feeding of shake-flasks as described above
**not assayed

EXAMPLE 4

Growth Enhancement of *E. coli* with pRED2

A typical high-cell density frementation is of a fed-batch type. The optimal rate of nutrient addition, and consequently the productivity, is ultimately limited by the rate at which cells can aerobically catabolize the carbon source without generating growth-inhibitory metabolites such as acetate and lactate (Zabriskie and Arucuri, *Factors influencing productivity of fermentations employing recombinant microorganisms*, Enzyme and Microbial Technology 8:706–717, 1986; Tsai et al, *The effect of organic nitrogen and glucose on the productivity of recombinant insulin-like growth factor in high cell density Escherichia coli fermentations*, Journal of Industrial Microbiology 2: 181–187, 1987). In this experiment, we compare the growth properties of the recombinant strain (JM101:pRED2) expressing Vitreoscilla hemoglobin with similar plasmid-containing (JM101:pUC9) and plasmid-free (JM101) strains under typical fed-batch fermentation conditions.

Materials and Methods

Cells were grown in a New Brunswick Microferm fermentor at 37°±0.5° C. and a pH of 7±0.05 with an initial working volume of 2.5 L. A constant air-flow rate of 4.5 L/min and agitator speed of 300 rpm were maintained throughout each run. Silicone antifoam AF60 was used to control foaming. The batch medium and feed medium 1 listed in Table 2 in Tsai et al, supra were used. Growth following inoculation was in batch mode. After batch stationary phase was reached, continuous feeding was initiated using feed medium 1 at a flow rate of 10 mL/hr. For plasmid-containing cells, 100 mg/L ampicillin was used. In all cases, the dissolved oxygen (DO) levels remained fairly constant around 5% of air saturation for most of the run except during the early log phase and towards batch stationary phase.

Results

The growth parameters measured for the three strains are listed below. Batch stationary phase refers to conditions before continuous feeding was started.

|  | JM101 | JM101:pUC9 | JM101:pRED2 |
|---|---|---|---|
| Batch log-phase growth rate ($h^{-1}$) | 0.95 | 0.73 | 0.95 |
| Batch stationary-phase dry cell mass (g/L) | 2.6 | 1.6 | 2.6 |
| Fed-batch log-phase growth rate ($h^{-1}$) | 0.056 | 0.033 | 0.066 |
| Final dry cell mass (g/L) | 5.8 | 2.8 | 5.9 |

Further, the respiratory behavior of JM101:pRED2 was improved compared to the control strains at low DO levels, as observed in a Gilson respirometer.

Conclusion

Cells containing Vitreoscilla hemoglobin grow faster and to higher densities than comparable plasmid-containing controls.

EXAMPLE 5

Expression of Vitreoscilla Hemoglobin (VHb) in *E. Coli* under the Regulation of Other Promoters In Examples 1, 3, and 4 above, the expression of hemoglobin is under the regulation of its native oxygen-regulated promoter. Hence, it is not possible to modulate independently the dissolved oxygen concentration (DO) and the intracellular VHb level. In order to overcome this, the inventors attempted to express this protein under the control of other regulatable promoters which are functional in *E. coli*, such as trp (Russell and Bennett, *Construction and analysis of in vitro activity of E. coli promoter hybrids and promoter mutants that alter the −35 to −10 spacing*, Gene 20:231–243, 1982) and tac (deBoer et al, *The tac promoter: a functional hybrid derived from the trp and lac promoters*, Proc. Natl. Acad. Sci. U.S.A. 80:21–25, 1983).

Materials and Methods

Plasmid pRED4 (see Example 2) was linearized with HindIII and treated with exonuclease Bal31 to generate 5'end deletions in the HindIII-SphI VHb fragment (Maniatis et al, supra). After digestion with SphI, the resulting VHb fragments were cloned into HindIII-SphI digested pUC19. The positions of the deleted end- pHbCAT (3.6 kb)

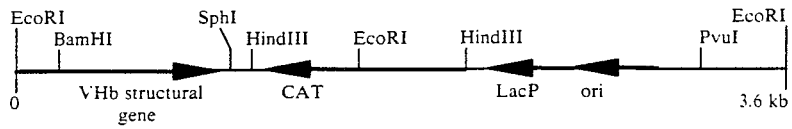

```
              EcoRI
5' GAATT CCCCT GTTGA CAATT AATCA TCGAA CTAGT TAACT AGTAC

BamHI
    GCAGC TTGGC TGCAG GTCGA CGGAT CCCGG GRCTA GAGGA AGTCT

Start codon of VHb

CATGT TAGAC . . . (same as in Example 3 up to SphI site)
``` trp and tac promoters and the chloramphenicol acetyl transferase gene (CAT) were purchased from Pharmacia, Inc. Oligonucleotides were synthesized at California Institute of Technology using an Applied Biosystems DNA synthesizer. All DNA enzymes were obtained from vendors.

The functional assay for the VHb gene product is as described in Webster and Liu, supra.

Cells were pelleted at 4° C. and resuspended in 100 mM Tris (pH 7.5), 50 mM NaCl. This cell suspension was sonicated at 75 W for 3 min. on ice. After spinning in at 12,000 g for 10 min., the supernatant was collected and assayed for VHb. Total protein content was estimated using the Bradford assay kit from BioRad Inc. VHb activity is reported as delta-$A_{419-436}$/mg total protein.

Results

One of the deletions, pRED302, mapped 2 base-pairs upstream of the ATG start codon for the VHb structural gene. This deletion was used for further work. The EcoRI/BamHI trp promoter cartridge was cloned upstream of the truncated VHb fragment. The following ribosome binding site was synthesized:

```
5' GATCCCGGGTCTAGAGGA 3'
   GGCCCAGATCTCCT
``` and inserted between the BamHI and nuclease-blunted XbaI sites to give rise to a trp promoter-controlled VHb expression system. The CAT gene (Alton and Vapnek, *Nucleotide sequence analysis of the chloramphenicol resistance transposon Tn9*, Nature 282:864–869, 1979) was inserted downstream and under the control of the lac promoter available on this pUC19-based plasmid. This gene product can be conveniently assayed (Neumann et al, *Novel rapid assay for chloramphenicol acetyltransferase gene expression*, BioTechniques 5:444–447, 1987) and hence serves as a useful reporter Finally, the β-lactamase gene on this pUC19-based plasmid was deleted by digestion and religation with PvuI. The purpose of this step is to eliminate the presence of a plasmid-encoded periplasmic protein. The plasmid thus obtained was called pHbCAT and was transformed into JM101. As a control, the CAT gene was cloned downstream and under the control of the lac promoter in puC19. The β-lactamase gene was identically deleted. This plasmid was called pCAT. The restriction maps and the anticipated sequence of relevant regions of these two plasmids are shown below.

The sequence of the region spanning between EcoRI and the start of the VHb structural gene is shown above. It includes the trp promoter and a synthetic ribosome binding site.

pCAT (2.5 kb)

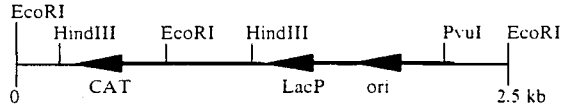

The effect of tryptophan (repressor) and indole acrylic acid (gratuitous inducer) on VHb levels in JM101/pHbCAT are shown in the Table below. In these experiments, cells were grown to mid-log in minimal medium containing 3 g/L glycerol, 3 g/L Casamino acids, and the appropriate amount of indole-acrylic acid or tryptophan.

| Host: Plasmid | Tryptophan (mg/L) | Indole-acrylic acid (mg/L) | Specific Hb Activity* |
|---|---|---|---|
| JM101/pCAT | — | — | $3.4 \times 10^{-3}$ |
| JM101/pHbCAT | 20 | — | $6.2 \times 10^{-3}$ |
| " | 4 | — | $18.3 \times 10^{-3}$ |
| " | — | — | $31.5 \times 10^{-3}$ |
| " | — | 1 | $29.8 \times 10^{-3}$ |
| " | — | 2.5 | $36.5 \times 10^{-3}$ |
| " | — | 5 | $47.0 \times 10^{-3}$ |
| " | — | 10 | $36.6 \times 10^{-3}$ |

Note:
*(delta-$A_{419-436}$/mg total soluble protein)

To express the VHb gene under the control of the tac promoter, an expression plasmid plasmid was made using a HindIII-BamHI tac promoter cartridge, the BamHI/SphI fragment from pHbCAT, and the HindIII-SphI digested fragment of the vector pBR322 (Bolivar et al, *Construction and characterization of new cloning vehicles. II. A multipurpose cloning system* Gene 2:95–113, 1977).

With this construct (pINT1), the level of redness of cells correlated well with varying amounts of the gratuitous inducer IPTG, indicating that the gene product synthesis was under the control of tac. The advantages of this expression system are:

a. Higher expression of VHb, and
b. Ability to use complex medium for growth.

EXAMPLE 6

Growth of *E. coli*—Expressing VHb under the Regulation of Other Promoters

The aim of this experiment was to demonstrate the growth effects of VHb on *E. coli*. In these cases, VHb is expressed using promoters different from the native VHb oxygen-regulated promoter. The strains:plasmids used are:

1. HB101:pBR322 (pBR322 from BRL)
2. JM101:pINT1 (pINT1 discussed in Example 5).

The two hosts have nearly identical genotypes, the major difference being the presence of an F' factor in JM101 which harbors the lacI$^q$ gene. This gene is necessary to keep a strong promoter like tac under control.

The following media recipes shall be henceforth referred to in the appropriate annotated form:

1X LB: 10 g/L Bactotryptone, 5 g/L Yeast Extract, 5 g/L NaCl, 3 g/L $K_2HPO_4$, 1 g/L $KH_2PO_4$, 100 mg/L Ampicillin 2X LB: 20 g/L Bactotryptone, 10 g/L Yeast Extract, 5 g/L NaCl, 3 g/L $K_2HPO_4$, 1 g/L $KH_2PO_4$, 100 mg/L Ampicillin 3X LB: 50 g/L Bactotryptone, 25 g/L Yeast Extract, 5 g/L NaCl, 3 g/L $K_2HPO_4$, 1 g/L $KH_2PO_4$, 100 mg/L Ampicillin.

The experiment was conducted as follows. Single colonies of the two strains listed above were inoculated into 5 mL 1X LB in a culture tube and grown overnight at 37° C.

0.5 mL of the appropriate inoculum was transferred into 250 mL culture flasks containing 50 mL medium as follows:

1) HB101:pBR322:2X LB
2) HB101:pBR322:5X LB
3) JM101:pINT1:2X LB
4) JM101:pINT1:2X LB+0.1 mM IPTG
5) JM101:pINT1:2X LB+0.5 mM IPTG
6) JM101:pINT1:5X LB
7) JM101:pINT1:5X LB+0.1 mM IPTG
8) JM101:pINT1:5X LB+0.5 mM IPTG

Cells were then grown for 24 h at 37° C. in a New Brunswick G24 Environmental Incubator Shaker with the shaker speed adjusted to medium setting. At the end of the experiment, the $OD_{600}$ was measured in a Spectronics 21 spectrophotometer by diluting the culture 10-fold in 1% NaCl. The data are listed below.

| Host/Plasmid | LB conc. | IPTG conc. (mM) | Final $OD_{600}$ |
|---|---|---|---|
| HB101:pBR322 | 2X | 0 | 3.00 |
| JM101:pINT1 | 2X | 0 | 3.03 |
| JM101:pINT1 | 2X | 0.1 | 2.91 |
| JM101:pINT1 | 2X | 0.5 | 3.00 |
| HB101:pBR322 | 5X | 0 | 2.73 |
| JM101:pINT1 | 5X | 0 | 3.26 |
| JM101:pINT1 | 5X | 0.1 | 3.40 |
| JM101:pINT1 | 5X | 0.5 | 3.15 |

From this data, the following conclusions may be drawn:

1. In all cases involving 2X LB, the cells grew to approximately the same density. This density is roughly twice that obtained routinely in 1X LB under similar growth conditions and indicates exhaustion of available nutrient. In other words, cells have entered stationary phase of growth due to nutrient limitation.

2. It has been demonstrated (Tsai et al., supra) that cells grown in excess nutrient eventually attain an oxygen-limited growth condition due to which they generate inhibitory metabolics such as acetate. Eventually, this leads to cessation of growth, even if more nutrient is supplied. The results of all 5X experiments are indicative of such an occurrence. In other words, oxygen limitation has arisen eventually, causing the culture to reach stationary phase.

3. Hence, it may be argued that under $O_2$-limited growth, the presence of the hemoglobin gene enhances the growth characteristics of *E. coli*. This result is similar to that in Examples 3 and 4, with the difference being that here VHb expression is not regulated by DO levels.

4. It appears that under the given growth conditions, there exists an optimal level of VHb expression that maximizes the growth enhancement effect. Such an optimum may be a function of specific growth properties of each cell line and/or plasmid construct as well as of the environmental conditions of growth. The optimum may thus have to be determined for different applications of this technology on a case-by-case basis; however, such determination does not require undue experimentation.

EXAMPLE 7

Effect of VHb Presence on the Synthesis of Another Cloned Protein in *E. coli*

The aim of this experiment was to demonstrate the effect of the VHb gene on the synthesis of a model cloned gene product. This is an important application of the technology, since a wide variety of gene products are produced commercially via recombinant DNA technology. A typical process of this kind involves a high cell density fed-batch fermentation. The productivity of such processes is ultimately limited by insufficient oxygen availability.

The following hosts/plasmids were used in this example:

1. JM101:pCAT
2. JM101:pHbCAT.

The construction of these plasmids is described in Example 5.

The following media compositions were used:

LB: 10 g/L Bactotryptone, 5 g/L Yeast Extract, 5 g/L NaCl, 3 g/L $K_2HPO_4$, 1 g/L $KH_2PO_4$, 30 mg/L Chloramphenicol 10X feed: 100 g/L Bactotryptone, 100 g/L Yeast Extract, 150 mg/L Chloramphenicol.

The experiment was conducted as follows:

Single colonies of the two strains were inoculated into 5 ml LB in a culture tube and grown overnight. 1 mL of the inoculum was transferred into 100 mL fresh LB and the growth curve was followed. As cells approached the end of log phase, a 1 mL pulse of 10X feed was added and the growth burst was followed. A second pulse was similarly added. At the end of this growth phase, a pulse of 1 mL 10X feed containing 100 mM IPTG was added to induce the expression of the CAT gene. One hour later, a sample was withdrawn for monitoring CAT activity. The results of the experiment are shown below.

| | JM101:pCAT | JM101:pHbCAT |
|---|---|---|
| 1) Klett before IPTG pulse | 670 | 700 |
| 2) Total soluble protein (mg/ml culture broth) | 0.31 | 0.435 |

-continued

| | JM101:pCAT | JM101:pHbCAT |
|---|---|---|
| 3) CAT activity (units/mg soluble protein) | $1.39 \times 10^4$ | $2.67 \times 10^4$ |
| 4) CAT activity (units/ml culture broth) | $4.3 \times 10^3$ | $11.6 \times 10^3$ |

From the above data, the following conclusions may be drawn.

1. The presence of VHb enhances the synthesis of a cloned gene product, even at low levels of VHb industrion.
2. Besides increasing the amount of cloned gene product per unit volume of culture, the presence of VHb may also enhance the specific activity (activity per unit amount of totally soluble protein) of the cloned gene product.

EXAMPLE 8

Oxygen-Dependent Regulation of Expression of VHb in *E. coli* by Native Vitreoscilla Hemoglobin Upstream Sequences The aims of this experiment were as follows:

1. To demonstrate that VHb gene expression in *E. coli* increases in response to decreasing oxygen levels in the medium.
2. To establish transcriptional-level regulation of gene expression.
3. To determine the sensitivity of this oxygen-dependent genetic switch in response to changes in dissolved oxygen concentrations.

The HindIII-SphI fragment containing the VHb gene and flanking sequences was cloned into the corresponding sites of the vector pBR322, thereby creating the plasmid pOX1. This was then transformed into the *E. coli* hold, HB101. The fermentation was conducted in a New Brunswick Bioflo II fermentor with a 2.5 L working volume using LB (10 g/L Bactotryptone, 5 g/L yeast extract, 5 g/L NaCl, 3 g/L $K_2HPO_4$, 1 g/L $KH_2PO_4$) plus 8 mg/L silicone antifoam as medium at 37° C., pH 7.0 with a constant agitation speed of 300 rpm. All other methods involve conventional protocols (Maniatis, et al., supra).

Cells were grown to an $OD_{600} \approx 0.25$ with DO maintained greater than 50% air saturation at all times. At this point, the air supply was gradually reduced so that the DO fell to about 1% air saturation in an almost linear manner over a period of 45 min. (i.e., a time scale long enough for gene induction, yet within approximately one generation time of *E. coli*). Samples were intermittently taken and analyzed for VHb mRNA and protein levels. Later, nitrogen was sparged in the vessel to study the induction of the VHb promoter under strictly anaerobic conditions.

Results

1. The level of VHb mRNA increased about ten-fold as DO dropped from 70% to 1% air saturation.
2. There was a corresponding increase in VHb activity. A lag was noticed between increase in VHb mRNA level and increase in the quantity of active VHb. This may occur because of the requirement of additional heme biosynthesis in the host cell in order to produce active VHb.
3. The VHb promoter was switched on to significant levels only below 40% air saturation and attains maximum induction levels below 5% air saturation.
4. The promoter switches off under strictly anaerobic conditions, indicating the importance of a basal level of aerobicity in the environment for maximal gene expression.

EXAMPLE 9

Oxygen-Dependent Expression of another Cloned Protein

In order to use the VHb oxygen-regulated promoter element (ORE) to express other genes, deletions were made from the cloned Vitreoscilla fragment described in Examples 1 and 2 to isolate a functional promoter element. The enzyme Bal 31 was employed for this purpose (Maniatis, et al., supra). One of the fragments isolated extended from the 5' end of the sequence listed in Example 2 to approximately 125 bp downstream, as sized on a 6% polyacrylamide gel. This fragment was used to express a gene different from that for VHb under oxygen-dependent regulation.

In this experiment, the fragment just described was fused to a promoterless chloramphenicol acetyl transferase (CAT) gene cartridge purchased from Pharmacia Inc. This fusion was inserted into the HindIII-SphI sites of the vector pBR322 to create the plasmid, pOX1. This was transformed into the *E. coli* host, HB101.

To test the functionality of the ORE, an experiment similar to that in Example 8 was conducted. CAT gene product assays were conducted using a conventional protocol (Neumann, et al., supra).

Results

At DO=70% air saturation, the CAT activity in *E. coli* HB101:pOX1 was $6.1 \times 10^4$ units/mg soluble protein. After maintaining the DO between 2 to 5% air saturation for 45 min., CAT activity in *E. coli* HB101:pOX1 was $6.3 \times 10^5$ units/mg soluble protein. This demonstrates the isolation of a functional ORE capable of expressing proteins other than Vitreoscilla hemoglobin under control of dissolved oxygen content of the culture.

EXAMPLE 10

Heterologous Expression of VHb in a Eucaryotic *Saccharomyces cerevisiae* Host

In this experiment, we attempted to express the VHb gene in a model eucaryote, *Saccharomyces cerevisiae*. The vector used was pBM 150 (Johnston and Davis, *Sequences that regulate the divergent GAL1-GAL10 promoter in Saccharomyces cerevisiae*, Molecular and Cellular Biology 4: 1440–1448, 1984) and the host strain was D603 (ade−, ura−, met−, lys−, reg 1), Srienc et al., *Effect of ARS1 mutations on chromosome stability in Saccharomyces cerevisiae*, Molecular and Cellular Biology 5:1676–1684, 1985. The truncated VHb structural gene referred to in Example 5 was cloned downstream of the GAL10 promoter to create plasmid pYRED1.

The recombinant strain D603:pYRED1 was significantly redder than the control D603:pBM150 when grown in the presence of galactose (2% peptone, 1% yeast extract, 2% galactose). Inocula were grown in minimal galactose medium Significant hemoglobin activity was determined in sonicates from D603:pYRED1 compared to D603:pBM150 controls based on the difference spectrum hemoglobin analysis referenced in Example 3.

EXAMPLE 11

Growth Enhancement of *Saccharomyces cerevisiae* Cells Expressing VHb

In this example, the effect of VHb expression on the growth of the yeast *Saccharomyces cerevisiae* was studied. The VHb gene was cloned into a yeast expression plasmid, AAH5, that is stably maintained as an extrachromosomal plasmid in yeast cells.

Materials and Methods

Plasmid pEX-2 was constructed as follows. The BamHI/SphI fragment described in Example 5 was cloned by blunt-end ligation into the HindIII site of the yeast expression vector AAH5 (Ammerer, *Expression of genes in yeast using the ADC1 promoter,* Methods in Enzymology 101:192-201, 1983). AAH5 contains the selectable yeast marker Leu 2, the 2 micron circle origin of replication, and a unique HindIII site flanked by the transcriptional promoter and terminator regions of the yeast alcohol dehydrogenase-1 (ADH-1) gene. The ADH-1 promoter will support high levels of transcription of any sequence cloned into the HindIII site. The ADH-1 gene is constitutively expressed in yeast.

*S. cerevisiae* strain 488-0 (leu2, ura3, his 1-7) was transformed with plasmids AAH5 and pEX-2 by the rapid colony transformation procedure (Keszenman-Pereyra and Heida, *A colony procedure for transformation of Saccharomyces cerevisiae,* Curr. Genet. 13:21-23, 1988), and plated on synthetic dextrose (SD) medium (Rose, *Isolation of genes by complementatuon in yeast,* Methods in Enzymology, 152: 481-504, 1987) without leucine. A representative clonal cell line from each transformation was established after colony purification of a primary transformant.

For the growth studies, single yeast colonies were inoculated into 2 mL of SD −leu (+leu for 488-0) and cultured for 24 hr at 260 rpm at 30° C. in a Labline Model 3258 Orbit Enviro-shaker. 0.5 mL of this inoculum was added to 50 mL of the same medium in a 250 mL flask and cultured at 260 rpm at 30° C. Cell growth was measured by turbidity ($A_{600\ nm}$) using a Perkin-Elmer Lambda 4A Spectrophotometer. When the glucose level of the culture medium dropped below 2.0 mM, the cultures were pulsed with 1/40 volume of a concentrated medium containing 20×SD (40% glucose, 13.3% Difco yeast nitrogen base without amino acids, and 1.6 mg/mL of all the amino acids except leucine. For strain 488-0, 1.6 mg/mL leucine was included in the pulse medium). Glucose concentration was estimated using Ames Glucostix test strips.

Results

A comparison of the growth curves of strains 488-0, 488-0:AAH5, and 488-0:pEX-2 grown under the above conditions revealed the following:

1. All three strains grew at an equivalent rate during the logarithmic stage of growth.

2. The VHb-containing strain 488-0:pEX-2 grew to a final optical density of 13.0, while strains 488-0:AAH5 and 488-0 grew to optical densities of only 10.0 and 9.5, respectively. This represents a 26.0% increase in final cell density between a strain carrying the VHb gene on a plasmid (488-0:pEX-2) compared to a strain containing the identical plasmid without the VHb gene (488-0:AAH5). In addition, this represents a 32.6% increase in the final cell density of 488-0:pEX-2 over the strain containing no AAH5-derived plasmid (488-0).

EXAMPLE 12

Growth Enhancement due to Expression of VHb in *E. coli* from a Chromosomically integrated gene In this example, the tac-VHb gene fusion, discussed in Example 5, was integrated into the chromosome of *E. coli* MG1655 (obtained from Cold Spring Harbor Laboratory, N.Y.).

Materials and Methods

A defective Tn10 transposon (Foster, et al., *Three Tn10-associated excision events: Relationship to transposition and role of direct and inverted repeats,* Cell, 23:215-227, 1981) was constructed as follows. A kanamycin resistance gene (Pharmacia Inc.) was cloned into the SalI site of pINTI (Example 5). The EcoRI/EagI fragment from the resulting plasmid, which contains the entire tac-VHb fusion and $Kan^R$ gene, was cloned between the inverted repeats (bases 1-66 on the right end and bases 9234-9300 on the left end) of a Tn10 derivative which lacks the transposase gene (obtained from Cold Spring Harbor Laboratory, N.Y.). The resulting element, Tn10dKan-tac-VHb, was cloned into a multicopy plasmid containing a tac-Tn10 rightward transposase (obtained from Cold Spring Harbor Laboratory, N.Y.). Transposition was induced with 0.5 mM IPTG for 4 hr, following which cells were plated on lactose-MaCConkey-Kan plates. Lac− mutants were selected and the transposon-induced mutation was induced into *E. coli* MG1655 using Pi phage (Silhavy et al., supra). One of the resulting Lac− colonies, which was further purified and checked for Lac−, $Kan^R$, $Amp^S$, VHb+ (IPTG inducible, as confirmed by assay described in Example 3), was designated GRO13. Comparison of growth properties of strains MG1655 and GRO13 in 2X LB (described in Example 6) containing 1 mM IpTG, followed by addition of a concentrated feed (25% Bactotryptone, 12.5% yeast extract), showed an increase in final cell densities (final cell densities: $OD_{600}=16.8$ for MG1655, $OD_{600}=18.1$ for GRO13).

What is claimed is:

1. A portable DNA sequence comprising the following DNA sequence, (reading 5' to 3', wherein the coding sequence is underlined), or a fragment of said sequence which is capable of acting as a promoter/regulator which is controlled by manipulating environmental oxygen, said fragment including the underlined translation initiator ATG:

AAGCTTAACG GACGCTGGGG TTAAAAGTAT TTGAGTTTTG ATGTGGATTA AGTTTTAAGA

GGCAATAAAG ATTATAATAA GTGCTGCTAC ACCATACTGA TGTATGGCAA AACCATAATA

ATGAACTTAA GGAAGACCCT C<u>ATGTTAGAC</u> <u>CAGCAAACCA</u> <u>TTAACATCAT</u> <u>CAAAGCCACT</u>

<u>GTTCCTGTAT</u> <u>TGAAGGAGCA</u> <u>TGGCGTTACC</u> <u>ATTACCACGA</u> <u>CTTTTTATAA</u> <u>AAACTTGTTT</u>

<u>GCCAAACACC</u> <u>CTGAAGTACG</u> <u>TCCTTTGTTT</u> <u>GATATGGGTC</u> <u>GCCAAGAATC</u> <u>TTTGGAGCAG</u>

```
CCTAAGGCTT TGGCGATGAC GGTATTGGCG GCAGCGCAAA ACATTGAAAA TTTGCCAGCT

ATTTTGCCTG CGGTCAAAAA AATTGCAGTC AAACATTGTC AAGCAGGCGT GGCAGCAGCG

CATTATCCGA TTGTCGGTCA AGAATTGTTG GGTGCGATTA AGAAGTATT GGGCGATGCC

GCAACCGATG ACATTTTGGA CGCGTGGGGC AAGGCTTATG GCGTGATTGC AGATGTGTTT

ATTCAAGTGG AAGCAGATTT GTACGCTCAA GCGGTTGAAT AAAGTTTCAG GCCGCTTTCA

GGACATAAAA AACGCACCAT AAGGTGGTCT TTTTACGTCT GATATTTACA CAGCAGCAGT

TTGGCTGTTG GCCAAAACTT GGGACAAATA TTGCCCTGTG TAAGAGCCCG CCGTTGCTGC

GACGTCTTCA GGTGTGCCTT GGCAT.
```

2. The DNA sequence of claim 1, wherein said portable DNA sequence further comprises a terminator.

3. The DNA sequence of claim 1, wherein said portable DNA sequence further comprises a leader sequence.

4. A substantially purified gene preparation comprising the portable DNA sequence of claim 1, operatively linked to the coding sequence for Vitreoscilla hemoglobin or to the coding sequence for a fragment of said hemoglobin having oxygen-binding activity, wherein said hemoglobin has the following amino acid sequence:

```
                    5                      10
        Met—Leu—Asp—Gln—Gln—Thr—Ile—Asn—Ile—Ile—
                   15                      20
        Lys—Ala—Thr—Val—Pro—Val—Leu—Lys—Glu—His—
                   25                      30
        Gly—Val—Thr—Ile—Thr—Thr—Thr—Phe—Tyr—Lys—
                   35                      40
        Asn—Leu—Phe—Ala—Lys—His—Pro—Glu—Val—Arg—
                   45                      50
        Pro—Leu—Phe—Asp—Met—Gly—Arg—Gln—Glu—Ser—
                   55                      60
        Leu—Glu—Gln—Pro—Lys—Ala—Leu—Ala—Met—Thr—
                   65                      70
        Val—Leu—Ala—Ala—Ala—Gln—Asn—Ile—Glu—Asn—
                   75                      80
        Leu—Pro—Ala—Ile—Leu—Pro—Ala—Val—Lys—Lys—
                   85                      90
        Ile—Ala—Val—Lys—His—Cys—Gln—Ala—Gly—Val—
                   95                     100
        Ala—Ala—Ala—His—Tyr—Pro—Ile—Val—Gly—Gln—
                  105                     110
        Glu—Leu—Leu—Gly—Ala—Ile—Lys—Glu—Val—Leu—
                  115                     120
        Gly—Asp—Ala—Ala—Thr—Asp—Asp—Ile—Leu—Asp—
                  125                     130
        Ala—Trp—Gly—Lys—Ala—Tyr—Gly—Val—Ile—Ala—
                  135                     140
        Asp—Val—Phe—Ile—Gln—Val—Glu—Ala—Asp—Leu—
                  145
        Tyr—Ala—Gln—Ala—Val—Glu.
```

5. The substantially purified gene preparation of claim 4, wherein the coding sequence for said Vitreoscilla hemoglobin has the following sequence:

```
ATGTTAGAC CAGCAAACCA TTAACATCAT CAAAGCCACT

GTTCCTGTAT TGAAGGAGCA TGGCGTTACC ATTACCACGA CTTTTTATAA AAACTTGTTT

GCCAAACACC CTGAAGTACG TCCTTTGTTT GATATGGGTC GCCAAGAATC TTTGGAGCAG

CCTAAGGCTT TGGCGATGAC GGTATTGGCG GCAGCGCAAA ACATTGAAAA TTTGCCAGCT

ATTTTGCCTG CGGTCAAAAA AATTGCAGTC AAACATTGTC AAGCAGGCGT GGCAGCAGCG

CATTATCCGA TTGTCGGTCA AGAATTGTTG GGTGCGATTA AGAAGTATT GGGCGATGCC

GCAACCGATG ACATTTTGGA CGCGTGGGGC AAGGCTTATG GCGTGATTGC AGATGTGTTT

ATTCAAGTGG AAGCAGATTT GTACGCTCAA GCGGTTGAA.
```

6. A recombinant DNA cloning vector comprising the portable DNA sequence of claim 1.

7. The recombinant DNA cloning vector of claim 6, further comprising a heterologous gene insert, the expression of which is under the control of said portable DNA sequence.

8. The vector of claim 7, wherein said vector is capable of replicating in a host cell grown in the presence of oxygen.

9. The vector of claim 6, wherein said vector is capable of replicating in host cells selected from the group consisting of microorganisms, cultured animal cells, cultured plant cells, and cultured insect cells.

10. The vector pUC19/pRED2.

11. A portable DNA sequence comprising the coding sequence for the Vitreoscilla hemoglobin protein or for a fragment of said protein having oxygen-binding activity, wherein said Vitreoscilla hemoglobin protein has the following sequence:

```
                5                          10
Met—Leu—Asp—Gln—Gln—Thr—Ile—Asn—Ile—Ile—

15                          20
Lys—Ala—Thr—Val—Pro—Val—Leu—Lys—Glu—His—

25                          30
Gly—Val—Thr—Ile—Thr—Thr—Thr—Phe—Tyr—Lys—

35                          40
Asn—Leu—Phe—Ala—Lys—His—Pro—Glu—Val—Arg—

45                          50
Pro—Leu—Phe—Asp—Met—Gly—Arg—Gln—Glu—Ser—

55                          60
Leu—Glu—Gln—Pro—Lys—Ala—Leu—Ala—Met—Thr—

65                          70
Val—Leu—Ala—Ala—Ala—Gln—Asn—Ile—Glu—Asn—

75                          80
Leu—Pro—Ala—Ile—Leu—Pro—Ala—Val—Lys—Lys—

85                          90
Ile—Ala—Val—Lys—His—Cys—Gln—Ala—Gly—Val—

95                         100
Ala—Ala—Ala—His—Tyr—Pro—Ile—Val—Gly—Gln—

105                         110
Glu—Leu—Leu—Gly—Ala—Ile—Lys—Glu—Val—Leu—

115                         120
Gly—Asp—Ala—Ala—Thr—Asp—Asp—Ile—Leu—Asp—

125                         130
Ala—Trp—Gly—Lys—Ala—Tyr—Gly—Val—Ile—Ala—

135                         140
Asp—Val—Phe—Ile—Gln—Val—Glu—Ala—Asp—Leu—

145
Tyr—Ala—Gln—Ala—Val—Glu.
```

12. A recombinant DNA cloning vector comprising the trp promoter operatively linked to the sequence claimed in claim 11.

13. A recombinant DNA cloning vector comprising the tac promoter operatively linked to the sequence claimed in claim 11.

14. A portable DNA sequence comprising the coding sequence for the Vitreoscilla hemoglobin protein or for a fragment of said protein having oxygen-binding activity, wherein the coding sequence of said Vitreoscilla hemoglobin protein is as follows:

```
                ATGTTAGAC CAGCAAACCA TTAACATCAT CAAAGCCACT

GTTCCTGTAT TGAAGGAGCA TGGCGTTACC ATTACCACGA CTTTTTATAA AAACTTGTTT

GCCAAACACC CTGAAGTACG TCCTTTGTTT GATATGGGTC GCCAAGAATC TTTGGAGCAG

CCTAAGGCTT TGGCGATGAC GGTATTGGCG GCAGCGCAAA ACATTGAAAA TTTGCCAGCT

ATTTTGCCTG CGGTCAAAAA AATTGCAGTC AAACATTGTC AAGCAGGCGT GGCAGCAGCG

CATTATCCGA TTGTCGGTCA AGAATTGTTG GGTGCGATTA AAGAAGTATT GGGCGATGCC

GCAACCGATG ACATTTTGGA CGCGTGGGGC AAGGCTTATG GCGTGATTGC AGATGTGTTT

ATTCAAGTGG AAGCAGATTT GTACGCTCAA GCGGTTGAA.
```

15. A recombinant DNA cloning vector comprising the trp promoter operatively linked to the sequence claimed in claim 14.

16. A recombinant DNA cloning vector comprising the tac promoter operatively linked to the sequence claimed in claim 14.

17. A method of preparing an active Vitreoscilla hemoglobin or a fragment of said hemoglobin having oxygen-binding activity, consisting essentially of:
  (a) preparing a portable DNA sequence which, upon expression, produces Vitreoscilla hemoglobin or a fragment of said hemoglobin having oxygen-binding activity;
  (b) introducing said sequence into a heterologous microbial host cell;
  (c) culturing said cell under conditions appropriate for expression of the protein; and
  (d) isolating the protein.

18. The method of claim 17 wherein said portable DNA sequence is integrated into the chromosome of said host cell.

19. The method of claim 17 wherein said portable DNA sequence is contained in a vector capable of replicating in said host cell.

20. The method of claim 19 wherein the vector containing said portable DNA sequence is pUC19/pRED2.

21. The method of claim 17 wherein the microbial host cell is selected from the group consisting of bacteria, fungi, molds, and yeast.

22. The method of claim 21 wherein said host cell comprises yeast.

23. The method of claim 22 wherein said vector containing said portable DNA sequence is pYRED1.

24. The microorganism *Escherichia coli* JM101 pUC19/pRED2, having ATCC accession number 67536.

25. A process for producing a DNA molecule containing a structural gene whose expression is controlled by manipulating environmental oxygen, comprising the step of operatively fusing an isolated structural gene to the portable DNA sequence of claim 1.

26. A process for controlling expression of a structural gene by manipulating environmental oxygen, comprising the steps of operatively fusing an isolated structural gene to the portable DNA sequence of claim 1, incorporating the operatively fused gene into a stable extrachromosomal element or the chromosome of a microbial host cell, and controlling the concentration of environmental oxygen available to said host cell.

27. A method for expressing any foreign protein in a host *E. coli* cultured cell, comprising:
  (a) introducing into said host cultured cell a vector comprising a portable DNA sequence according to claim 1, operatively fused to a foreign DNA sequence coding for said foreign protein; and (b) growing said host cultured cell in an appropriate medium and environment for expression of said protein and isolating the protein expressed by said foreign DNA.

28. The method of claim 27, wherein said portable DNA sequence operatively fused to said foreign sequence is integrated into the chromosome of said host cell.

29. A method for preparing any foreign protein in a microbial cell, comprising:
 (a) introducing into said cell a replicable vector comprising the portable DNA sequence of claim 1 operatively linked to the coding sequence for said protein;
 (b) growing said cell at a first level of environmental oxygen;
 (c) lowering the level of environmental oxygen to a second level which activates expression of the promoter/regulator of the portable DNA sequence.

30. A method for preparing any foreign protein in a microbial cell, comprising:
 (a) introducing into said cell the portable DNA sequence of claim 1 operatively linked to the coding sequence for said protein, such that said sequence is integrated into the chromosome of said cell;
 (b) growing said cell at a first level of environmental oxygen;
 (c) lowering the level of environmental oxygen to a second level which activates expression of the promoter/regulator of the portable DNA sequence.

31. A method for enhancing the growth or yield of products from a microbial cell culture grown in the presence of oxygen, comprising:
 (a) preparing a portable DNA sequence encoding Vitreoscilla hemoglobin protein or fragment thereof having oxygen-binding activity;
 (b) introducing said portable DNA sequence into a microbial host cell;
 (c) culturing the host cell under conditions appropriate for expression of the protein and production of an active oxygen-binding protein.

* * * * *